(12) United States Patent
Sawant et al.

(10) Patent No.: US 7,786,304 B2
(45) Date of Patent: Aug. 31, 2010

(54) PROCESS FOR THE PREPARATION OF ESZOPICLONE

(75) Inventors: Shrikant Dattatraya Sawant, Mumbai (IN); Anil Mahadev Naik, Mumbai (IN); Girish Arvind Kavishwar, Mumbai (IN); Smita Girish Kavishwar, Mumbai (IN)

(73) Assignee: Centaur Pharmaceutical Pvt. Ltd., Mumbai (IN)

( * ) Notice: Subject to any disclaimer, the term of this patent is extended or adjusted under 35 U.S.C. 154(b) by 0 days.

(21) Appl. No.: 11/979,573

(22) Filed: Nov. 6, 2007

(65) Prior Publication Data

US 2008/0146800 A1 Jun. 19, 2008

(30) Foreign Application Priority Data

Nov. 6, 2006 (IN) .................... 1841/MUM/2006
May 3, 2007 (IN) .................... 852/MUM/2007
Jul. 17, 2007 (IN) .................... 1367/MUM/2007

(51) Int. Cl.
*C07D 471/00* (2006.01)
(52) U.S. Cl. .................................................... 544/350
(58) Field of Classification Search ................... 544/350
See application file for complete search history.

(56) References Cited

U.S. PATENT DOCUMENTS 3,862,149 A * 1/1975 Cotrel et al. ................. 544/238
6,319,926 B1 * 11/2001 Cotrel et al. ................. 514/249
2007/0054914 A1 * 3/2007 Mandava et al. ............ 514/249

\* cited by examiner

*Primary Examiner*—James O Wilson
*Assistant Examiner*—Douglas M Willis

(57) ABSTRACT

The invention relates to a process for making 6-(5-chloro-2-pyridinyl)-6,7-dihydro-7-oxo-5H-pyrrolo-[3,4-b]pyrazin-5-yl-4-methyl piperazine-1-carboxylate, also known as zopiclone. The invention further describes an effective method for resolving zopiclone into its enantiomers (eszopiclone and (R)-zopiclone) and also provides a method of recycling of (R)-zopiclone. The process for making (S)-6(S)-6-(5-chloro-2-pyridinyl)-6,7-dihydro-7-oxo-5H-pyrrolo-[3,4-b]pyrazin-5-yl-4-methyl piperazine-1-carboxylate (eszopiclone), comprises reacting 2-amino 5-chloropyridine with pyrazine 2,3, dicarboxylic acid anhydride at room temperature to obtain 3-(5-chloropyrid-2-yl)carbamoyl-2-pyrazine-2-carboxylic acid; cyclizing the 3-(5-chloropyrid-2-yl)carbamoyl-2-pyrazine-2-carboxylic acid in a second inert organic solvent to obtain 6-(5-chloropyrid-2-yl)5,7-dioxo-5,6-dihydropyrrolo [3,4-b]-pyrazine; reducing the 6-(5-chloropyrid-2-yl)5,7-dioxo-5,6-dihydropyrrolo[3,4-b]-pyrazine to obtain 6-(5-chloropyrid-2-yl)-5-hydroxy-7-oxo-5,6-dihydropyrrolo-[3,4-b] pyrazine; pyrazine with 1-chlorocarbonyl-4-methylpiperazine hydrochloride in a third organic solvent in presence of triethyl amine along with a catalytic amount of an acylation catalyst to obtain racemic zopiclone; e) recrystallizing the zopiclone from an alkyl ester solvent followed by purifying in suitable alcohols or mixtures thereof; and resolving the racemic zopiclone by treating with (+)-O—O' dibenzoyl tartaric acid to obtain eszopiclone.

10 Claims, No Drawings

PROCESS FOR THE PREPARATION OF ESZOPICLONE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISK

Not Applicable

BACKGROUND OF THE INVENTION

1. Field of the Invention

This invention relates to a reproducible process for the preparation of 6-(5-chloro-2-pyridinyl)-6,7-dihydro-7-oxo-5H-pyrrolo-[3,4-b]pyrazin-5-yl-4-methyl piperazine-1-carboxylate also known as zopiclone and it's intermediate 6-(5-chloropyridyl-2-yl)-5-hydroxy-7-oxo-5,6 dihydropyrrolo[3,4-b]pyrazine. The said invention further relates to an effective method for resolution of zopiclone into its enantiomers and furthermore provides a method of recycling of (R)-zopiclone.

2. Description of the Related Art 6-(5-chloro-2-pyridinyl)-6,7-dihydro-7-oxo-5H-pyrrolo-[3,4-b]pyrazin-5-yl-4-methyl piperazine-1-carboxylate, known as zopiclone under its international non-proprietary name, is a hypnotic agent of cyclopyrrolone class possessing a pharmaceutical profile similar to that of benzodiazepines and having high efficacy and low toxicity. The S-enantiomer or (+) zopiclone is less toxic, more active than its other enantiomer and is currently sold under the brand name of Lunesta for the treatment of insomnia. Zopiclone can be represented by Formula-I and was disclosed in U.S. Pat. No. 3,862,149 in its racemic form.

Formula I

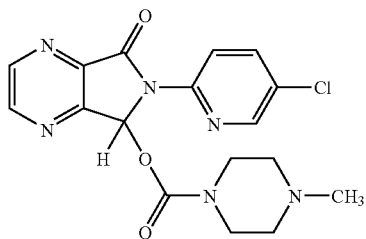

The process for preparing Zopiclone and its intermediate were first disclosed in U.S. Pat. No. 3,862,149 and U.S. Pat. No. 4,220,646. A method of treating sleep disorders in a human using (+) Zopiclone substantially free from (−) zopiclone are described in U.S. Pat. No. 5,786,357 and WO/93/10788 respectively.

U.S. Pat. No. 3,862,149 describes a process for preparing zopiclone. The process comprises reacting 2-amino-5-chloropyridine with pyrazine 2,3-dicarboxylic acid anhydride to obtain 3-(5-chloropyrid-2-yl)carbamoyl-pyrazine-2-carboxylic acid, which is further treated with thionyl chloride to obtain 6-(5-chloropyrid-2-yl)-5,7-dioxo-5,6-dihydro-5H-pyrrolo[3,4-b]pyrazine 6-(5-chloropyrid-2-yl)-5,7-dioxo-5,6-dihydro-5H-pyrrolo[3,4-b]pyrazine is reduced using potassium borohydride in a mixture of dioxane and water followed by neutralization with acetic acid to obtain 6-(5-chloropyrid-2-yl)-5-hydroxy-7-oxo-5,6-dihydro-5H-pyrrolo[3,4-b]-pyra-zine. The reaction of 6-(5-chloropyrid-2-yl)-5-hydroxy-7-oxo-5,6-dihydro-5H-pyrrolo[3,4-b]pyra-zine with 1-chlorocarbonyl-4-methyl piperazine in anhydrous dimethyl formamide and sodium hydride (50% dispersion in mineral oil) yields the final product, Zopiclone.

The above reaction involves multistage synthesis and many intermediates resulting in poor yields of the final product zopiclone. Further, thionyl chloride is toxic, corrosive, a potential lachrymator and also difficult to handle when used on an Industrial scale.

CZ 288047 discloses a process for making a zopiclone intermediate 6-(5-chloropyrid-2-yl)-5-hydroxy-7-oxo-5,6-dihydropyrrolo[3,4-b]-pyrazine, which comprises a selective reduction of 6-(5-chloropyrid-2-yl)-5,7-dioxo-5,6-dihydropyrrolo[3,4-b]-pyrazine by using potassium borohydride in liquid organic amide in the presence of water at a temperature of 70° C. However, this process discloses neither selectivity nor yield and purity of product.

In Indian Published Patent Application No. 645/MUM/2004 discloses the reaction of pyrazine-2,3-dicarboxylic acid with acetic anhydride and concomitant reaction with 2-amino-5-chloro pyridine at a temperature of 120-130° C. in a mole ratio 1.23:1 to obtain 6-(5-chloropyrid-2-yl)-5,7-dioxo-5,6-dihydropyrrolo[3,4-b]pyrazine, which is selectively reduced with sodium borohydride in the presence of organic solvent-water system. The product, 6-(5-chloropyrid-2-yl)-5-hydroxy-7-oxo-5,6-dihydropyrrolo[3,4-b]pyrazine (V) is reacted with 1-chlorocarbonyl-4-methyl piperazine in pyridine and methylene chloride system to yield 6-(5-chloro-2-pyridinyl)-6,7-dihydro-7-oxo-5H-pyrrolo-[3,4-b]pyrazin-5-yl-4-methyl piperazine-1-carboxylate (zopiclone).

US2007/0054914A1 describes the reaction of 6-(5-chloropyridyl-2-yl)-5-hydroxy-7-oxo-5,6-dihydropyrrolo[3,4-b]pyrazine and 1-chlorocarbonyl-4-methylpiperazine hydrochloride using an inorganic base and phase transfer catalyst in a mixture of organic solvents and water at −80 to 50° C. The obtained zopiclone is recrystallized from suitable solvent/solvent mixtures followed by resolution of racemic zopiclone using an enantiomerically pure di-toluoyl tartaric acid or its hydrates to obtain eszopiclone.

In some of these process steps, the reactants, per se, are the same but employ varying conditions to achieve better purity or yield. Although some of the problems are solved by modifying the reaction conditions or route of synthesis as taught by the prior art, there still exists problems like polymerization of intermediates due to the lengthy reaction periods and high temperatures, which need to be investigated.

The sodium hydride isopotential hazardous due to problems associated with handling on a large scale. The reactant, 1-chlorocarbonyl-4-methylpiperazine as a base on a commercial scale is unstable (Ref. US patent 2007/0054914 A1) as well as commercial unavailable. The use of pyridine on a large scale poses environmental hazards.

The process for resolving zopiclone is described in EP609210, wherein racemic zopiclone is dissolved along with D(+)-O,O'-dibenzoyl tartaric acid in methylene chloride to obtain diastereomeric dibenzoyl tartrate salt, followed by recrystallization in 44 volumes of acetonitrile, then followed by two recrystallizations from 17 volumes of methylene chloride-acetonitrile mixture (47:53) to obtain pure diastereomeric salt with an overall yield of 36%. The eszopiclone (crude) is isolated from dibenzoyl tartaric acid salt followed by recrystallization from acetonitrile yields pure eszopiclone with an overall yield of 23%. The main disadvantage of this process is the use of large volumes of solvent mixtures, which is difficult to recover.

There remains a need to provide an alternative to the prior art processes, which is cost-effective, feasible and highly reproducible on an industrial scale with high yield and purity, which has become the subject matter of the present invention.

BRIEF DESCRIPTION OF THE SEVERAL VIEWS OF THE DRAWINGS(S)

Not Applicable

BRIEF SUMMARY OF THE INVENTION

The main objective of this invention is to provide an environment friendly and industrially reproducible process without involving the hazardous chemicals, thus minimizing operational problems. Also, the process is efficient and cost-effective as the solvents are recoverable and recyclable.

The invention discloses a process for preparing eszopiclone ((S)-zopiclone) using the following steps:

a) reacting 2-amino 5-chloropyridine with pyrazine 2,3-dicarboxylic acid anhydride in a molar ratio of 1.05:1, in an inert organic solvent, at room temperature to obtain 3-(5-chloropyrid-2-yl)carbamoyl-2-pyrazine-2-carboxylic acid;

b) cyclizing the 3-(5-chloropyrid-2-yl)carbamoyl-2-pyrazine-2-carboxylic acid in an inert organic solvent in presence of triethyl amine and ethylchloroformate to obtain 6-(5-chloropyrid-2-yl) 5,7-dioxo-5,6-dihydropyrrolo[3,4-b]-pyrazine;

c) reducing the 6-(5-chloropyrid-2-yl)5,7-dioxo-5,6-dihydropyrrolo[3,4-b]-pyrazine, preferably in a conventional manner, to obtain 6-(5-chloropyrid-2-yl)-5-hydroxy-7-oxo-5,6-dihydropyrrolo-[3,4-b]pyrazine;

d) reacting 6-(5-chloropyrid-2-yl)-5-hydroxy-7-oxo-5,6-dihydropyrrolo[3,4-b]pyrazine with 1-chlorocarbonyl-4-methylpiperazine hydrochloride in an organic solvent in presence of triethyl amine along with a catalytic amount of an acylation catalyst to obtain racemic zopiclone;

e) dissolving racemic zopiclone along with (+)-O—O'-dibenzoyl tartaric acid in methylene chloride solvent to obtain a mixture of diastereomeric salt of dibenzoyl tartaric acid;

f) recrystallization of the crude diastereomeric salt in an organic solvent, preferably a single solvent, such as acetonitrile; and g) isolating eszopiclone from desired dextrorotatory dibenzoyl tartrate salt followed by recrystallizing from a suitable organic solvent.

In a further aspect, the invention provides a method to recycle (R)-zopiclone, which remains as a waste product (R)-zopiclone is isolated from the reaction mass and subjected to acid/base hydrolysis to obtain 6-(5-chloropyrid-2-yl)-5-hydroxy-7-oxo-5,6-dihydro-pyrrolo-[3,4-b]pyrazine, which is further reacted with 1-chlorocarbonyl-4-methylpiperazine hydrochloride to obtain zopiclone as mentioned above. Zopiclone thus obtained is further resolved to obtain the desired isomer of eszopiclone.

DETAILED DESCRIPTION OF PRESENTLY PREFERRED EMBODIMENTS

The description of invention is given in detail with certain preferred and optional embodiments, so that various aspects thereof may be more fully understood and appreciated.

The invention provides an improved process for preparation of zopiclone and furthermore describes an effective method for resolving racemic zopiclone to obtain eszopiclone with high enantiomeric purity and yield.

According to one embodiment, the key intermediate 6-(5-chloropyrid-2-yl) 5,7-dioxo-5,6-dihydropyrrolo[3,4-b]-pyrazine (A) is prepared having a good yield and purity (>99%) by cyclizing 3-(5-chloropyrid-2-yl)carbamoyl-pyrazine-2-carboxylic acid (III) using ethyl chloroformate and triethylamine in a suitable inert organic solvent, preferably methylene dichloride at a temperature of 0 to 5° C. (Scheme I). This process is cost-effective and easy to carry out on industrial scale as the reaction goes to completion at low temperature within an hour. This low temperature reaction also allows the complete recovery of the solvent used in the said process.

The compound, 3-(5-chloropyrid-2-yl)carbamoyl-pyrazine-2-carboxylic acid (II) is prepared by reacting pyrazine 2,3 dicarboxylic acid anhydride (II) with 2-amino-5-chloropyridine in an inert organic solvent, preferably, methylene chloride at room temperature.(Scheme I).

The addition of 2-amino-5-chloropyridine to pyrazine 2,3-dicarboxylic acid anhydride (II) in a lot wise manner at room temperature in a molar ratio of 1.05:1 surprisingly accelerates the reaction to completion in resulting the product, 3-(5-chloropyrid-2-yl)carbamoyl-pyrazine-2-carboxylic acid (III) having high purity (>99%) with a good yield of 85 to 90% when compared with the prior art processes.

Pyrazine 2,3-dicarboxylic acid anhydride (II) is obtained by reacting pyrazine-2,3-dicarboxylic acid (I) with acetic anhydride at a temperature of 100-120° C.

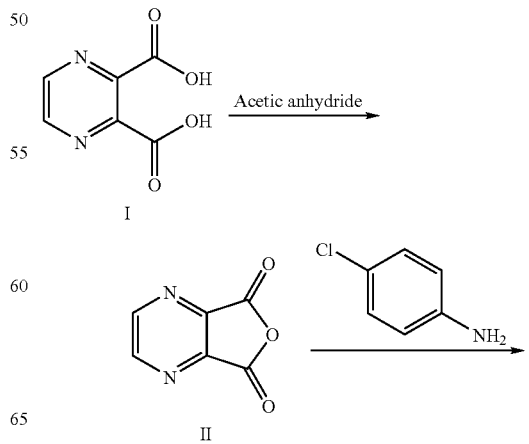

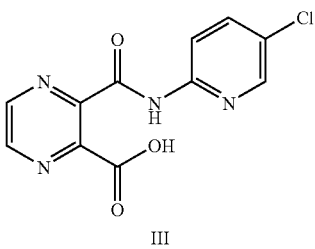

III

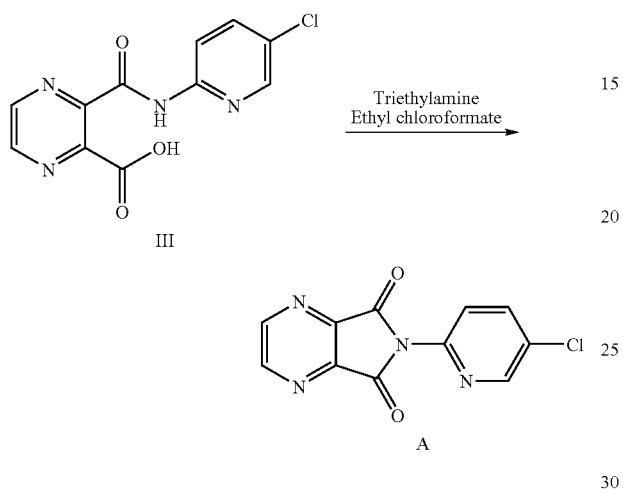

Alternatively, the intermediate, 6-(5-chloropyrid-2-yl) 5,7-dioxo-5,6-dihydropyrrolo[3,4-b]-pyrazine (A) can be prepared in one pot without isolating the 3-(5-chloropyrid-2-yl) carbamoyl-pyrazine-2-carboxylic acid (III) as shown in scheme II.

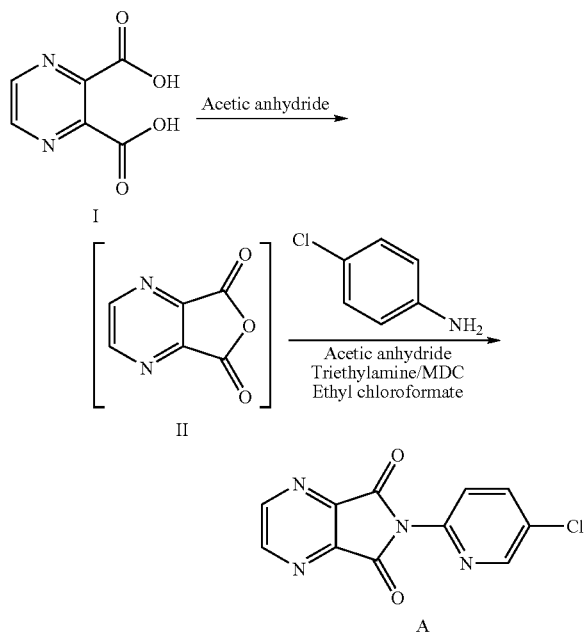

In another embodiment, 6-(5-chloropyrid-2-yl)-5-hydroxy-7-oxo-5,6-dihydropyrrolo-[3,4-b]pyrazine is prepared by reducing the intermediate, 6-(5-chloropyrid-2-yl)5,7-dioxo-5,6-dihydropyrrolo[3,4-b]-pyrazine obtained as above, in a conventional manner.

In a further embodiment, the compound, 6-(5-chloropyrid-2-yl)-5-hydroxy-7-oxo-5,6-dihydropyrrolo-[3,4-b]pyrazine, is reacted with 1-chlorocarbonyl-4-methylpiperazine hydrochloride in a suitable organic solvent in the presence of triethyl amine and acylation catalyst such as N,N-dimethylamino pyridine to obtain zopiclone (Scheme III) in high yields. The byproduct, triethylamine hydrochloride formed in the reaction is removed through normal workup procedure.

Scheme III

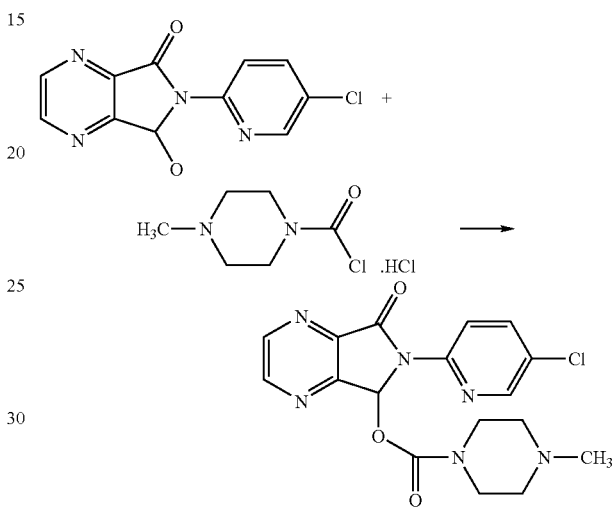

The use of N,N-dimethylamino pyridine in catalytic amount accelerates the alkylation reaction. The use of N,N-dimethylamino pyridine along with triethylamine provides distinct advantages in terms of operational efficiency/safety on a large scale.

The suitable solvent used for the above reaction (Scheme-III) is selected from methylene chloride or dimethylformamide. The reaction can be conveniently carried out at a temperature of 0 C to 42° C.

The crude zopiclone isolated is and further crystallized from ethyl acetate; the crystallized product is further purified using isopropanol to obtain zopiclone with high HPLC purity and good yields.

In yet another embodiment, the zopiclone obtained from the above is subjected to chiral resolution to isolate the required eszopiclone with high optical purity. The racemate resolution can be carried out at a temperature of 0° C. to the boiling point of the solvent used. It is simplest to work at room temperature.

Accordingly, racemic zopiclone is preferably reacted with a resolving agent (+)-O,O'-dibenzoyl tartaric acid in methylene dichloride at room temperature to obtain the diastereomeric salt (Scheme IV) which is crystallized from acetonitrile followed by conversion into eszopiclone by treating with an inorganic base, such as NaOH. Eszopiclone thus obtained has a purity above 99%. Eszopiclone is recrystallized from ethyl acetate to obtain the product with purity of 99.9%

In accordance with the above process, the racemic zopiclone is reacted with (+)—O,O'-dibenzoyl tartaric acid in an organic solvent, followed by complete distillation of the solvent to obtain a mixture consisting of diastereomeric salt of zopiclone (H) in Scheme II.

Scheme IV

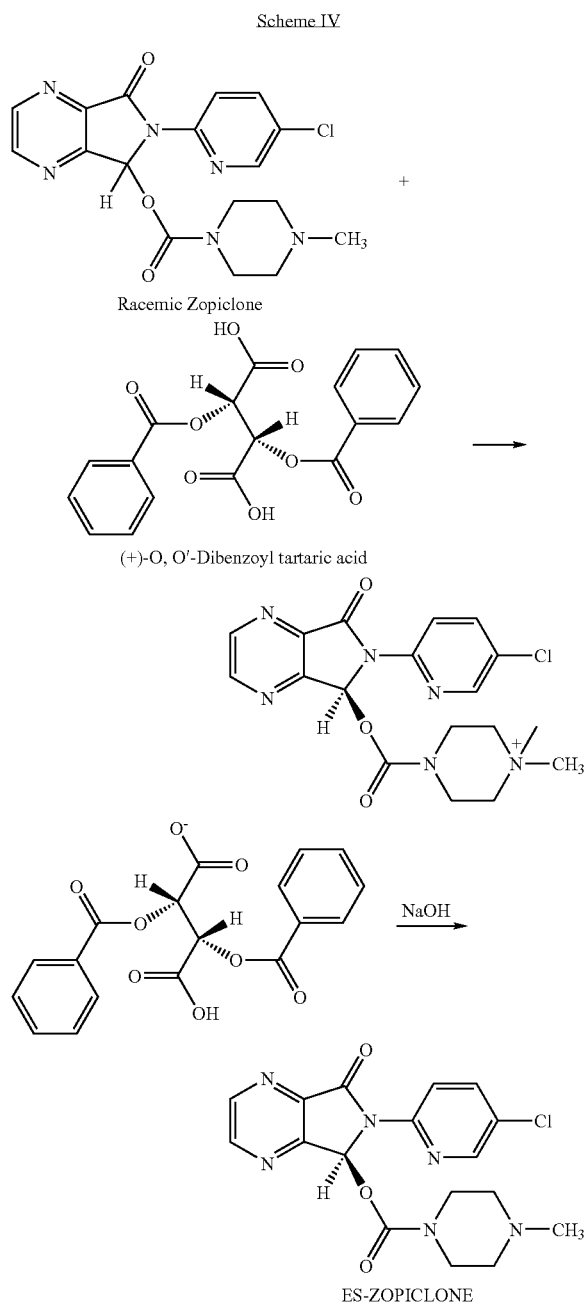

The suitable organic solvents used for the salt formation can be selected from alkyl/aryl acetates, aliphatic alcohols, aliphatic/aromatic hydrocarbons, aliphatic/cyclic ethers, chlorinated solvents such as methylene dichloride, chloroform or chlorobenzene. One preferred solvent is methylene dichloride.

The (+)-O,O'-dibenzoyl tartaric acid can be employed as a monohydrate or in anhydrous form. The salt formation can be effected at ambient temperature or at elevated temperature. Typically, the step of resolution is carried out at a temperature range of 0° C. to 80° C. or the reflux temperature of the solvent, for a period ranging between 1-24 hours, to obtain zopiclone (+)-O,O'-dibenzoyl tartrate salt.

Recrystallization of dibenzoyl tartrate salt obtained as above is performed in single organic solvent at a temperature ranging between 0° C.-80° C. Thus, the crude diastereomeric salt from the residue is recrystallized twice using acetonitrile alone as a single solvent to obtain single diastereomeric salt, thereby leaving behind (R)-zopiclone in acetonitrile solution.

The dextrorotatory isomer of zopiclone can be obtained from its dibenzoyl tartrate salt by neutralizing it using an inorganic base followed by extraction into an organic solvent like methylene dichloride. The bases suitable for neutralizing the diastereomeric salt include sodium hydroxide, potassium hydroxide, sodium carbonate, potassium carbonate, etc. The distillation of methylene dichloride followed by addition of suitable alkyl ester precipitates out the crude eszopiclone having enantiomeric purity of 99%.

Accordingly, crystallization of crude eszopiclone from ethyl acetate gives eszopiclone having enantiomeric purity of more than 99.9% by HPLC. Thus, the inventors have avoided the use of acetonitrile in the purification of final product, which is very difficult to remove during the drying process.

In another embodiment, the invention provides a process to recycle the (R)-zopiclone, which remains in solution as waste product. (R)-zopiclone is recovered from the solution by any known conventional methods, for example, by solvent distillation, evaporation, or precipitation by adding a non-polar solvent, etc. This is followed by neutralization with base, extraction using methylene chloride followed by removal of the solvent. The (R)-isomer isolated is subjected to acid hydrolysis using aqueous HCl, obtaining 6-(5-chloropyrid-2-yl)-5-hydroxy-7-oxo-5,6-dihydropyrrolo-[3,4-b]pyrazine.

The compound, 6-(5-chloropyrid-2-yl)-5-hydroxy-7-oxo-5, 6-dihydropyrrolo-[3,4-b]pyrazine, is reacted with 1-chlorocarbonyl-4-methylpiperazine hydrochloride in a suitable organic solvent in the presence of triethyl amine and N,N-dimethylamino pyridine to obtain zopiclone in high yields. The racemate thus obtained is further resolved to obtain eszopiclone by the above stated method.

Without further description, it is believed that one of ordinary skill in the art can, using the preceding description and the following illustrative examples, make and utilize the compounds of the present invention and practice the claimed methods. The following examples are given to illustrate the present invention. It should be understood that the invention is not to be limited to the specific conditions or details described in this example.

EXAMPLE 1

Preparation of 3-(5-chloropyrid-2-yl)carbamoyl-pyrazine 2 carboxylic acid

In a clean, dry 500 ml R. B. flask charged acetic anhydride (162 gms) and pyrazine-2,3, dicarboxylic acid (50 gins). The reaction mass was heated to 100-120° C. up to completion of reaction. After completion of the reaction, the excess acetic anhydride was distilled under vacuum. Charged methylene dichloride (350 ml) to the above reaction mass followed by 2-amino-5-chloropyridine (40 gms) in a lot wise manner at room temperature for 30 min. The reaction mass was stirred at room temperature for 2 hrs; the reaction mixture was cooled to 5-10° C. for 1 hr. The reaction mixture was filtered and washed with chilled methylene dichloride to obtain 3-(5-chloropyrid-2-yl)carbamoyl-pyrazine-2-carboxylic acid.

Yield=82 gms.

EXAMPLE 2

Preparation of 6-(5-chloropyrid-2-yl) 5,7-dioxo-5,6-dihydropyrrolo[3,4-b]-pyrazine In a clean 500 ml R. B. flask charged pyrazine-2,3-dicaroxylic acid (50 gms) and acetic anhydride (162 gms). The reaction mass was heated to 110-120° C. till the completion of reaction to get pyrazine-2,3-dicarboxylic acid anhydride. After completion of the reaction, excess acetic anhydride was distilled out under vacuum and furthermore charged with methylene dichloride (315 ml) and 2-amino-5-chloropyridine (40 gms) in a lot wise manner at room temperature for 30 min. Further, the reaction mixture was stirred for 2 hours at room temperature. The reaction mass was cooled to 5 to 10° C. for one hour, the product was filtered and washed with chilled methylene dichloride. The solid was charged with methylene dichloride (235 ml), triethylamine (40.9 ml) at a temp. of 0-5° C. followed by ethyl chloroformate (28.1 ml). The reaction mass was stirred at 0-5° C. for 1 hr, water (200 ml) was added to the reaction mixture and the mass stirred at room temperature for 1 hr to obtain the solids. The title compound thus separated was isolated by filtration.

Yield=65 gms.

The HPLC purity of this product was above 99%.

EXAMPLE 3

Preparation of Zopiclone

Charged 1.0 Kg (3.81 moles) of 6-(5-chloropyridyl-2-yl)-5-hydroxy-7-oxo-5,6-dihydro-pyrrolo[3,4b]pyrazine in 10.0 L. of methylene chloride, and the reaction mixture was cooled to 5-10° C. 1.0 Kg of 1-chlorocarbonyl-4-methylpiperazine hydrochloride was added at the same temperature. 1.22 Kg (12 moles) of triethyl amine was added to the reaction mixture followed by adding N,N-dimethylamino pyridine (0.035 Kg) at temperature 5-10° C. in two lots. The reaction mixture was heated to reflux and maintained for 2 hrs. Reaction mixture was cooled to room temperature and 4.5 L. of water was added at 25° C. The organic layer was separated and the aqueous phase was extracted with methylene dichloride (2.0 L). The combined organic phase was washed with water (2.0 L), the organic phase was separated and concentrated at an atmospheric pressure to obtain crude zopiclone. The crude zopiclone was recrystallized from ethyl acetate and further purified from isopropanol (Yield: 1.2 Kg).

EXAMPLE 4

Preparation of Eszopiclone

Racemic zopiclone (1.0 Kg; 2.57 mol) and D (+)-O,O'-dibenzoyl tartaric acid monohydrate (0.98 Kg) were charged in dichloromethane (10 Lit.). The solution was stirred at room temperature for 3 hrs. After completion of the reaction (monitored by TLC), the reaction mixture was concentrated under a reduced pressure to obtain the crude salt (1.9 kg). The crude salt was obtained by being recrystallised twice from acetonitrile (57.0 L & 9.5 L) at the reflux temperature to obtain the dextrorotatory diastereomer salt of zopiclone. The (R) isomer of zopiclone remains in acetonitrile solution.

Yield of the isolated diastereomeric salt—1.0 Kg.

The above isolated diastereomer salt (1.0 Kg) was dissolved in a mixture of methylene dichloride (10 L.) and water (2 L). 2N sodium hydroxide solution was added to the reaction mixture at 5-10° C. until a pH 10-11 was reached. The organic phase was separated and aqueous phase was extracted using methylene dichloride (3 L). The combined organic phase was washed with water and the solvent distilled out. To this, ethyl acetate (1.5 L) was added and the reaction mass was chilled. The crude eszopiclone precipitated out was then filtered and further purified from ethyl acetate to obtain 0.36 Kg of pure eszopiclone with enantiomeric purity more than 99.9% by HPLC.

EXAMPLE 5

Recycling of (R)-zopiclone and its Conversion to Eszopiclone (R)-Zopiclone (50 g) was dissolved in 10% HCl (500 ml) and heated up to 70° C. for 3 hrs. The progress of the reaction was monitored by TLC. After completion of the reaction, the reaction mass was cooled to room temperature, further cooled to 0° C. to 5° C. and filtered to obtain 6-(5-chloropyrid-2-yl)-5-hydroxy-7-oxo-5,6-dihydro-pyrrolo-[3,4-b]pyrazine. (22.4 g). Charged 22.4 g of 6-(5-chloropyridyl-2-yl)-5-hydroxy-7-oxo-5,6-dihydro-5H-pyrrolo[3,4-b]pyrazine in 250 ml of methylene chloride and the reaction mixture cooled to 5-10° C. 22.4 g of 1-chlorocarbonyl-4-methylpiperazine hydrochloride was added at the same temperature. 27.32 g of triethyl amine was added to the reaction mixture followed by addition of N,N-dimethylamino pyridine (0.8 gms) at temperature 5-10° C. in two lots. Reaction mixture was heated to reflux and maintained for 2 hrs. Reaction mixture was cooled to room temperature and 100 ml. of water was added at 25° C. The organic layer was separated and aqueous phase was extracted with methylene chloride (50 ml). The combined organic phase was washed with water (50 ml), the organic phase was separated and concentrated at atmospheric pressure to obtain crude zopiclone. The crude zopiclone was recrystallised from ethyl acetate and further purified from isopropanol (Yield: 26.8 gms). The racemic zopiclone thus obtained was resolved using the method given in example 4 to obtain eszopiclone.

Although certain presently preferred embodiments of the invention have been specifically described herein, it will be apparent to those skilled in the art to which the invention pertains that variations and modifications of the various embodiments shown and described herein may be made without departing from the spirit and scope of the invention. Accordingly, it is intended that the invention be limited only to the extent required by the appended claims and the applicable rules of law.

What is claimed is:

1. A process for preparing (S)-6-(5-chloro-2-pyridinyl)-6,7-dihydro-7-oxo-5H-pyrrolo-[3,4-b]pyrazin-5-yl-4-methyl piperazine-1-carboxylate (eszopiclone), comprising the steps of:
   a) reacting, in a single pot, 2-amino 5-chloropyridine with pyrazine-2,3-dicarboxylic acid anhydride in a molar ratio of 1.05:1, in a first inert organic solvent, at room temperature to obtain 3-(5-chloropyrid-2-yl)carbamoyl-2-pyrazine-2-carboxylic acid;
   b) cyclizing, in a single pot, the 3-(5-chloropyrid-2-yl) carbamoyl-2-pyrazine-2-carboxylic acid in a second inert organic solvent in presence of triethyl amine and ethylchloroformate to obtain 6-(5 chloropyrid-2-yl)-5,7-dioxo-5,6-dihydropyrrolo[3,4-b]pyrazine;

c) reducing the 6-(5-chloropyrid-2-yl)-5,7-dioxo-5,6-dihydropyrrolo[3,4-b]pyrazine to obtain 6-(5-chloropyrid-2-yl)-5-hydroxy-7-oxo-5,6-dihydropyrrolo[3,4-b]pyrazine;

d) reacting 6-(5-chloropyrid-2-yl)-5-hydroxy-7-oxo-5,6-dihydropyrrolo[3,4-b]pyrazine with 1-chlorocarbonyl-4-methylpiperazine hydrochloride in a third organic solvent in a presence of triethyl amine along with a catalytic amount of an acylation catalyst to obtain racemic zopiclone;

e) recrystallizing the zopiclone from an alkyl ester solvent followed by purifying in suitable alcohols; and f) resolving the racemic zopiclone by treatment with (+)-O—O'-dibenzoyltartaric acid to obtain eszopiclone.

2. The process of claim 1, wherein, the first inert organic solvent used in step a) and the second inert organic solvent used in step b) are methylene chloride.

3. The process of claim 1, wherein, step b) is carried out at a temperature of 0° C. to 5° C.

4. The process of claim 1, wherein, step d) is carried out at a temperature of 0° C. to 42° C.

5. The process of claim 1, wherein the third organic solvent used in step d) is selected from the group consisting of methylene chloride and N,N'-dimethylformamide.

6. The process of claim 1, wherein the acylation catalyst used in step d) is N,N'-dimethylaminopyridine.

7. The process of claim 1, wherein the alkyl ester of step e) is ethyl acetate and the alcohol of step e) is isopropanol.

8. The process of claim 1, wherein step e) comprises the steps of: 1) treating the racemic zopiclone with (+)-O—O'-dibenzoyltartaric acid in methylene chloride solvent to obtain the diastereomeric dibenzoyl tartaric acid salt; 2) recrystallizing the crude diastereomeric salt in acetonitrile to obtain diastereomeric salt of eszopiclone leaving behind (R)-zopiclone in the solution; 3) isolating eszopiclone from desired dextrorotatory dibenzoyl tartrate salt followed by recrystallizing from a fourth organic solvent; and 4) recycling of (R)-zopiclone to eszopiclone.

9. The process of claim 8, wherein the solvent used for recrystallization in step 3) is ethyl acetate.

10. The process of claim 8, wherein steps 1) to 4) are carried out at 0° C. to 80° C.

* * * * *